United States Patent [19]

Berglund

[11] Patent Number: 5,362,886

[45] Date of Patent: Nov. 8, 1994

[54] ASYMMETRIC SYNTHESIS

[75] Inventor: Richard A. Berglund, Lafayette, Ind.

[73] Assignee: Eli Lilly and Company, Indianapolis, Ind.

[21] Appl. No.: 135,032

[22] Filed: Oct. 12, 1993

[51] Int. Cl.$^5$ ............... C07D 333/16; C07C 41/05; C07C 43/20

[52] U.S. Cl. .................... 549/75; 568/630; 568/631

[58] Field of Search ............... 549/75; 568/630, 631

[56] References Cited

U.S. PATENT DOCUMENTS 5,023,269  6/1991  Robertson et al. ............... 514/438
5,068,451 11/1991  Lin et al. ............... 568/442

OTHER PUBLICATIONS

Berge et al., "Pharmaceutical Salts," J. Pharm. Sci., vol. 66, No. 1, 1977, pp. 1–19.
CA 116(1): 105979t, Nishikubo et al., "Solvent and Catalyst Effects On Addition Reaction of Phenyl Glycidyl Ether With S–Phenyl Thiocetate," Nippon Kagaku Kaishi 1991, (11), 1506–1513.
Deeter, et al., *Tetrahedron Letters*, 31(49), 7101–7104 (1990).
Wong, et al., *Life Sciences*, 43, 2049–2057 (1988).
Reinheimer, et al., *J. Am. Chem. Soc.*, 83, 2873–2877 (1961).
Reinheimer, et al., *J. Chem. Soc.*, 80, 164–168 (1958).

*Primary Examiner*—Glennon H. Hollrah
*Assistant Examiner*—Mary C. Cebulak
*Attorney, Agent, or Firm*—Joseph A. Jones

[57] ABSTRACT

This invention provides a stereospecific process for the synthesis of (S)-(+)-N,N-dimethyl-3-(1-naphthalenyloxy)-3-(2-thienyl)propanamine, a key intermediate in the synthesis of duloxetine.

7 Claims, No Drawings

ASYMMETRIC SYNTHESIS

BACKGROUND OF THE INVENTION

This invention belongs to the fields of pharmaceutical chemistry and synthetic organic chemistry, and provides an asymmetric process for the synthesis of a key intermediate in the preparation of duloxetine, (+)-N-methyl-3-(1-naphthalenyloxy)-3-(2-thienyl)propanamine, hydrochloric acid salt.

Duloxetine is a pharmaceutical now under development as an anti-depressant. It inhibits the uptake of both norepinephrine and serotonin and is presently in clinical evaluation. The compound was disclosed in U.S. Pat. Nos. 5,023,269 and 4,956,388 by Robertson, et al., and the synthesis of it was discussed in more detail by Deeter, et al., in *Tetrahedron Letters*, 31(49), 7101-04 (1990). The process for preparing duloxetine is there outlined as follows.

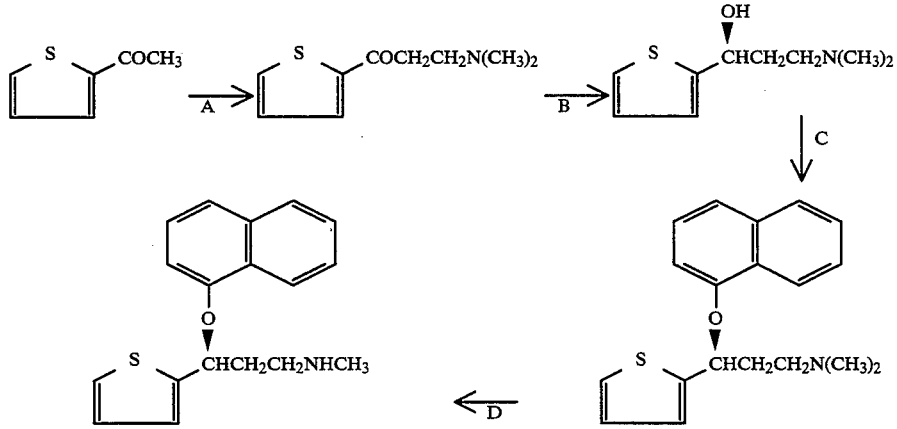

The product of Step D above, when in the hydrochloride salt form, is duloxetine.

The present invention provides improved conditions for carrying out Step C in the above scheme, whereby the product of Step C is obtained more quickly in better purity and yield than has previously been possible.

A particularly useful salt for the isolation of the intermediate is also provided.

SUMMARY OF THE INVENTION

The present invention provides a process for preparing (S)-(+)-N,N-dimethyl-3-(1-naphthalenyloxy)-3-(2-thienyl)propanamine comprising reacting (S)-(−)-N,N-dimethyl-3-(2-thienyl)-3-hydroxypropanamine with sodium hydride, potassium benzoate or potassium acetate, and 1-fluoronaphthalene in an organic solvent; and if desired, recovering the product as the phosphoric acid salt. The phosphoric acid salt is also an aspect and an embodiment of the invention.

DESCRIPTION OF THE PREFERRED EMBODIMENT

The present invention provides an asymmetric process for preparing the specific enantiomer shown above as the product of Step C in the scheme. It is named as the (S)-(+) enantiomer and that nomenclature will be used throughout this document. The starting material for the process of this invention, the hydroxypropanamine, is named as the (S)-(−) enantiomer.

The preferred solvent for carrying out the present invention is dimethylsulfoxide. Other solvents, such as dimethylformamide, pyridine and the like, may be used as well. The process may be effectively carried out at unusually high concentrations, such as from about 0.5–1.0 molar, preferably 0.6–0.9 molar. However, the rate and yield of the process is not seriously affected by the concentration, so long as the solubility limit is not exceeded, of course.

The order and manner of combining the reactants are not important and may be varied. The reactants may be added to the reaction mixture as solids, or may be dissolved individually and combined as solutions. Further any of the reactants may be dissolved together as subgroups, and those solutions may be combined in any order.

A preferred manner of carrying out the invention is to dissolve the starting material and sodium hydride together, add the potassium compound, and then add the 1-fluoronaphthalene, and that embodiment will be further described in detail.

When the starting material has been dissolved, preferably at ambient temperature such as from about 10° to about 35° C., a portion of sodium hydride is added. The amount of sodium hydride is equimolar with the starting material; no particular advantage is found in using excess sodium hydride. The reaction mixture is then stirred for a period, such as from about 5 to about 60 minutes, and then combined with potassium benzoate or potassium acetate and 1-fluoronaphthalene.

Only a small amount of the potassium compound is needed, from about 0.05 to about 1 equivalent. In general, the advantages of the present invention are best obtained when only from about 0.1 to about 0.3 equivalent of the potassium compound is used. There is no disadvantage is using more, except the obvious cost disadvantage.

An additional period of stirring is provided after the addition of the potassium compound, and then the 1-fluoronaphthalene is added. A small amount of excess 1-fluoronaphthalene, such as from about 1% to about 25% excess, may advantageously be used to assure consumption of the more expensive thiophene starting material.

When the fluoronaphthalene has been added, the reaction mixture is preferably warmed, to a temperature from about 40° to about 75° C., preferably from about 45° to about 70° C., and most preferably from about 60° to about 65° C., and the mixture is stirred for a short period of time, such as from about 1 to about 5 hours, most preferably from about 1.5 to about 4 hours.

The desired product is then isolated by conventional extractions and filtrations, and, if it is desired to do so, the product may advantageously be converted to the phosphoric acid salt by reaction with phosphoric acid in an organic solvent such as ethyl acetate.

The advantage of the present invention is found in its ability to prepare the desired product in yields in the range of 95%, with very little racemization, in short periods of time as described above. Previous procedures took more than a day, and gave product of inferior purity.

The hydroxypropanamine which is the starting material for the present process is available by the teachings of the prior art, but preparation 1 below is provided to assure its availability to the reader of the present document.

The product of the present process, the dimethyl compound, is converted to duloxetine by demethylating to provide the desired monomethyl pharmaceutical, and conversion to the hydrochloride salt. Preparation 2 below illustrates that conversion, which, like the preparation of the hydroxy starting material, is from the prior art and forms no part of the present invention.

PREPARATION 1

(S)-(−)-N,N-dimethyl-3-hydroxy-3-(2-thienyl)-propanamine

A mixture of 8.18 g of 2-acetylthiophene, 6.66 g of dimethylamine hydrochloride, 2.9 g of paraformaldahyde and 0.31 g of concentrated hydrochloric acid in 20 ml of isopropanol was heated to reflux and stirred for 6 hours. The mixture was then cooled to 0° C. and stirred for one hour more. The slurry was then filtered, and the solid was washed with cold ethanol. The washed solid was dried for 16 hours at 50° C. to obtain 12.5 g of 2-thienyl 2-dimethylaminoethyl ketone hydrochloride, as a white solid. A 12.0 g portion of that intermediate product was stirred in 40 ml of ethanol at ambient temperature, and the pH of the solution was raised to 11-12 by slow addition of sodium hydroxide. A 1.03 g portion of sodium borohydride was added, and the mixture was stirred at ambient temperature for 4 hours. Then 7.5 ml of acetone was added, and the mixture was stirred for 20 minutes more. The mixture was then concentrated by evaporation to a white slurry, and 120 ml of methyl t-butyl ether was added. The mixture was acidified to pH 1-1.5 by addition of concentrated hydrochloric acid, and the solution was stirred for ten minutes. The pH was then made basic to pH 12 by slow addition of sodium hydroxide.

The layers were then separated, the aqueous phase was extracted with 30 ml of methyl t-butyl ether, and the organic phases were combined and washed once with 50 ml of water. The organic phase was concentrated by evaporation to 118 ml, and was heated to 50° C.

In a separate vessel, (S)-(+)-mandelic acid, 4.18 g, was dissolved in 12 ml of ethanol at 50° C., and the mandelic acid solution was added slowly to the previous solution. The resulting slurry was then heated to reflux and stirred for 45 minutes. It was then cooled to ambient temperature, stirred for one hour, and filtered, and the solid was washed with methyl t-butyl ether. The solid was then dried under vacuum at 50° C. to obtain 7.29 g of the mandelic acid salt of the desired product, which is isolated as the free amine by dissolution in water, basification with sodium hydroxide solution, extraction into an organic solvent, and evaporation to remove the solvent.

EXAMPLE 1

(S)-(+)-N,N-dimethyl-3-(1-naphthalenyloxy)-3-(2-thienyl)propanamine, phosphoric acid salt A 13.5 g portion of (S)-(−)-N,N-dimethyl-3-hydroxy-3-(2-thienyl)propanamine was dissolved in 80 ml of dimethylsulfoxide at 25° C. To the solution was slowly added 3 g of sodium hydride as a 60% dispersion in mineral oil, with vigorous stirring. After 15 minutes of stirring, 1.17 g of potassium benzoate was added and stirring was continued at approximately constant temperature for another 15 minutes. Then, 12.8 g of 1-fluoronaphthalene was slowly added to the reaction mixture, and after the addition was complete, the mixture was heated and was stirred for 2.5 hours at 60°–65° C. The mixture was then poured slowly into 190 ml of cold water and the DH was adjusted to 4.8 by addition of acetic acid. The temperature of the mixture was brought to 25° C., and 75 ml of hexane was added and stirring was continued for 10 minutes. The layers were then separated and the aqueous phase was stirred again with 75 ml of hexane and the phases separated. The pH of the aqueous phase was adjusted to 10.2 by addition of aqueous sodium hydroxide, and 75 ml of ethyl acetate was added. That mixture was stirred for 15 minutes at 25° C., and the 2-phase mixture was vacuum filtered through a pad of filter aid. The phases of the filtrate were allowed to separate, and the aqueous phase was extracted with 75 ml of ethyl acetate. The extract was combined with the previous ethyl acetate layer, and that mixture was washed with 100 ml of water. The organic layer was stirred at 25° C., and to it was added, dropwise, 7 g of 85% phosphoric acid. After the addition was complete, the mixture was stirred for 20 minutes more and was then cooled to 0° C. and stirred for 1 hour at that temperature. The slurry was then filtered and the solids washed three times with 20 ml portions of cold ethyl acetate. The solid was dried at 60° C. to afford 24.19 g of the title compound as a white solid, 98.1% potency, adjusted yield 79.6%, 91% EE.

Assay Methodology

The product of the example was analyzed by high performance liquid chromatography, using a Spectra Physics SP 8800 instrument equipped with a SP 4400 integrator and a Spectroflow 757 detector, set at 230 nm, at a sensitivity of 0.5 absorption units, 1 second filter rise time. The column was a Dupont Zorbax Rx C8, 4.6 mm×25 cm. The eluant was 70% acetonitrile, 30% 0.01 M phosphate buffer at pH 6, flow rate of 1.0 ml/minute, injection volume 20 microliters. The samples were prepared by diluting 0.1 to 0.3 g of reaction mixture or extract to 50 ml with 1:1 acetonitrile:water. The product peak elutes at 13–17 minutes; starting material at 6–8 minutes; fluoronaphthalene at 5–6 minutes; dimethylsulfoxide at 2–3 minutes; and potassium benzoate at 2–2.5 minutes.

When a chiral assay was to be done, the same equipment was set at 280 nm and a sensitivity of 0.1 absorption unit, and a Chiralcel OD column was used. The eluant for chiral assays was 2% isopropanol, 0.2% diethylamine, and 97.8% hexane. The same injection and flow settings were used. The samples were prepared by diluting 0.1–0.3 g of reaction mixture or extract to 5 ml with dichloromethane, washing the mixture with about 5 ml of water, and drying the organic phase over sodium sulfate. The resulting solution was filtered and diluted to 25 ml with eluant. The desired enantiomer elutes at 5-5.5 minutes, the undesired enantiomer at 6-6.5 minutes and fluoronaphthalene at 3-4 minutes.

EXAMPLE 2

(S)-(+) -N, N-dimethyl -3- (1-naphthalenyloxy)-3-(2-thienyl)propanamine

A 1.60 g portion of (S)-(−)-N,N-dimethyl-3-hydroxy-3-(2-thienyl)propanamine was dissolved in 8 ml of dimethylsulfoxide at ambient temperature, to which was added 0.35 g of sodium hydride as a 60% dispersion in mineral oil with vigorous stirring. After 30 minutes of stirring, 0.28 g of potassium benzoate was added, and stirring was continued for 10 minutes more. Then 1.52 g of 1-fluoronaphthalene was added and the mixture was then stirred at 50° C. for 8 hours. The reaction mixture was poured slowly into 30 ml of cold water, and the pH was adjusted to 4.8 by addition of acetic acid. Fifteen ml of hexane was added, the mixture was stirred for 10 minutes, and the layers were separated. The aqueous phase was stirred again with 15 ml of hexane and the phases separated. The pH of the aqueous phase was adjusted to 12.5 by addition of aqueous sodium hydroxide, and 15 ml of ethyl acetate was added. The basic mixture was stirred at ambient temperature for 10 minutes, and the layers were separated. The aqueous phase was extracted with another 15 ml portion of ethyl acetate, and the organic extracts were combined, washed once with 30 ml of water, and dried over magnesium sulfate. The solvent was removed under vacuum to obtain a red-brown oil which was dissolved in the minimal amount of 1:1 ethyl acetate:hexane. The solution was flushed through a pad of silica gel using as eluant, ethyl acetate:hexane:methanol:amonium hydroxide, 47:47:5.8:0.2. The product fraction was evaporated under vacuum to obtain 2.3 g of the desired product as an amber oil.

Preparation 2

(S)-(+)-N-methyl-3-(1-naphthalenyloxy)-3-(2-thienyl)propanamine hydrochloride

Five g of the product of Example 1 was stirred in a mixture of 40 ml of toluene and 40 ml of water at 40° C., and 2.5 ml of 30% ammonium hydroxide solution was added. The mixture was stirred for 10 minutes at constant temperature and the layers were separated. The organic phase was washed with water, dried with magnesium sulfate and filtered. The filtrate was concentrated to half volume under vacuum and was heated to 55° C. Then 0.16 g of diisopropylethylamine was added, followed by the dropwise addition of 2.39 g of phenyl chloroformate. The mixture was stirred at 55° C. for 1.25 hours, and 50 ml of 1% sodium bicarbonate solution was added. The mixture was stirred for ten minutes at 40°-50° C., and the phases were separated. The organic phase was washed twice with 0.5 N hydrochloric acid, and then washed with 1% sodium bicarbonate solution. The washed organic phase was divided in half, and one aliquot was evaporated under vacuum and 26 ml of dimethylsulfoxide was added to the residue. The mixture was heated to 45° C., and 1 g of sodium hydroxide and 6 ml of water was added dropwise. The basic mixture was stirred for 18 hours at 50° C., diluted with 17 ml of water, and acidified to pH 5.0-5.5 by addition of acetic acid. Then 20 ml of hexane was added, the mixture was stirred for ten minutes, and the phases separated. The aqueous phase was made basic to pH 10.5 by addition of 50% aqueous sodium hydroxide, and 17 ml of ethyl acetate was added. After stirring for 10 minutes, the phases were separated, and the aqueous layer was extracted with another 17 ml of ethyl acetate. The combined organic extracts were washed with water and concentrated to 10 ml under vacuum. 0.46 g of concentrated hydrochloric acid was added to the residue, and then a seed crystal and an additional 10 ml of ethyl acetate was added. The mixture was stirred for 30 minutes more, and the solution was concentrated to 10 ml under vacuum. The residue was stirred for 1 hour at ambient temperature and 1 hour at 0° C. to produce a slurry, which was filtered. The solid was washed with chilled ethyl acetate to obtain 1.32 g of the desired product, which was duloxetine as a white solid of potency 99.8%.

The above Example illustrates the convenience and the excellent results of the present process.

I claim:

1. A process for preparing (S)-(+)-N,N-dimethyl-3-(1-naphthalenyloxy)-3-(2-thienyl)propanamine comprising reacting (S)-(−)-N,N-dimethyl-3-(2-thienyl)-3-hydroxypropanamine with sodium hydride, a potassium compound chosen from potassium benzoate or potassium acetate, and 1-fluoronaphthalene in an organic solvent.

2. A process of claim 1 wherein the product is recovered as the phosphoric acid salt.

3. A process of claim 1 wherein the (S)-(−)-N,N-dimethyl-3-(2-thienyl)-3-hydroxypropanamine is dissolved with the sodium hydride in the organic solvent, the potassium compound is then added with stirring and then the 1-fluoronaphthalene is added with additional stirring.

4. A process of claim 3 wherein the product is isolated as the phosphoric acid salt.

5. A process of claim 1 wherein the potassium compound is potassium benzoate.

6. A process of claim 3 wherein the potassium compound is potassium benzoate.

7. A process of claim 4 wherein the potassium compound is potassium benzoate.

* * * * *